United States Patent
Sadlo

[11] Patent Number: 5,857,466
[45] Date of Patent: Jan. 12, 1999

[54] PROPHYLACTIC

[76] Inventor: Frank C. Sadlo, P.O. Box 32222, Louisville, Ky. 40232

[21] Appl. No.: 766,625

[22] Filed: Dec. 13, 1996

Related U.S. Application Data

[60] Provisional application No. 60/008,694 Dec. 15, 1995.

[51] Int. Cl.$^6$ ........................................................ A61F 6/04
[52] U.S. Cl. ............................................. 128/844; 128/918
[58] Field of Search ..................................... 128/918, 842, 128/844; 604/347–353; 206/69

[56] References Cited

U.S. PATENT DOCUMENTS

| | | | |
|---|---|---|---|
| 4,872,464 | 10/1989 | Loeb | 128/844 |
| 5,094,250 | 3/1992 | Hessel | 128/844 |
| 5,531,230 | 7/1996 | Bell | 128/844 |
| 5,662,214 | 9/1997 | Wood | 128/844 |

FOREIGN PATENT DOCUMENTS

| | | | |
|---|---|---|---|
| 2622792 | 5/1989 | France | 128/918 |
| 3914186 | 10/1990 | Germany | 128/918 |

*Primary Examiner*—Michael A. Brown
*Attorney, Agent, or Firm*—Tod R. Nissle, P.C.

[57] ABSTRACT

A prophylactic apparatus reduces the risk that a venereal disease will be transmitted during sexual intercourse and reduces the risk that the prophylactic will, in use, cause physical injury. The prophylactic is provided in a wide variety of differing sizes one of which best correlates to the needs of each particular user.

3 Claims, 1 Drawing Sheet

5,857,466

PROPHYLACTIC

This application derives from the provisional patent application Serial No. 60/008,694, filed Dec. 15, 1995.

This invention relates to a prophylactic.

More particularly, the invention relates to a prophylactic apparatus which reduces the risk that a venereal disease will be transmitted during sexual intercourse and reduces the risk that the prophylactic will, in use, cause physical injury.

Prophylactics, or condoms, have long been utilized during sexual intercourse to prevent the transmission of venereal disease. Such prophylactics are typically fabricated from latex and have a generally cylindrical shape with a closed end and an open end. Prior to packaging, each prophylactic is rolled from the open end toward the closed end in a well known conventional fashion. In use, the prophylactic is installed by placing the rolled prophylactic on the distal end of an erect penis and unrolling the prophylactic down over the length of the penis. In many cases, the prophylactic can not be completely unrolled, and a rolled portion remains at the base of the penis. Although prophylactics have been useful in reducing the incidence of venereal disease, several disadvantages have long been associated with their use. First, prophylactics are marketed in two sizes, a "regular" size and a "large" size. Medical studies indicate that regular prophylactics have a circumference which is too large for about 15% of the male population, and also to have a length which is too long for about 50% of the male population (resulting in a rolled portion after the prophylactic is installed). Large prophylactics are too small for others in the male population. The inability of some men to use a prophylactic increases the incidence of AIDS and other venereal diseases. Second, the rolled portion which remains after a prophylactic is installed tends to roll back up the penis and further, even when the rolled portion stays in position, produces a tourniquet effect which pinches and causes vascular and neurological impairment of the functioning of the penis. One reason that the rolled portion of an installed prophylactic tends to roll back up the penis is that the base of the penis flares.

Accordingly, it would be highly desirable to provide an improve prophylactic which would decrease the incidence of venereal disease and would reduce the risk of physical injury during use of the prophylactic.

Therefore, it is a principal object of the invention to provide an improved prophylactic.

A further object of the invention is to provide an improved prophylactic which minimizes the likelihood that nerve endings in the base of a penis will be injured during use of the prophylactic.

Another object of the invention is to provide an improved prophylactic which reduces the risk that the prophylactic will move off the penis during use.

Still a further object of the invention is to provide an improved prophylactic which can be utilized by each adult male in the population.

Yet another object of the invention is to provide prophylactic apparatus which enables a male to determine the shape and dimension of prophylactic which will, when used, reduce the risk of injury and of transmission of venereal disease.

These and other, further and more specific, objects and advantages of the invention will be apparent to those skilled in the art from the following detailed description thereof, taken in conjunction with the drawings, in which.

Figure 1:
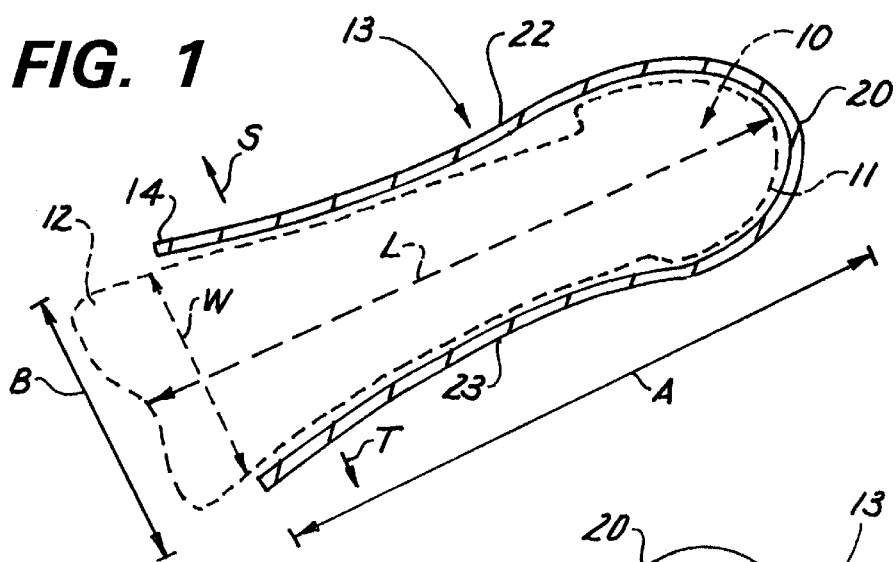
FIG. 1 is a side section view illustrating an elastic latex prophylactic constructed and used in accordance with the principles of the invention.

Briefly, in accordance with my invention, I provide an article of manufacture comprising a plurality of packages each including at least one condom. A first one of the packages includes first length indicia indicating the length of the condom in the package, and includes first width indicia different from the length indicia and indicating the width of the condom in the package. A second one of the packages includes second length indicia indicating the length of the condom in the second one of the packages, and includes second width indicia different from the length indicia on the second one of the packages and indicating the width of the condom in the second one of the packages. The first length indicia is different from the second length indicia and the first width indicia is different from the second width indicia to indicate that the length and width of the condom in the first package is different from the length and width of the condom in the second package. A third one of said packages includes third length indicia indicating the length of the condom in the third one of the packages, and third width indicia indicating the width of the condom in the third one of the packages. The third length indicia is equal to the second length indicia and the third width indicia is different from the second width indicia to indicate that the length of the condom in the third package is the same as the length of the condom in the second package and that the width of the condom in the third package differs from the width of the condom in the second package. A fourth one of the packages includes fourth length indicia indicating the length of the condom in the fourth one of the packages, and fourth width indicia indicating the width of the condom in the fourth one of the packages. The fourth length indicia is different from the second length indicia and the fourth width indicia is equal to the second width indicia to indicate that the length of the condom in the fourth package differs from the length of the condom in the second package and that the width of the condom in the fourth package is the same as the width of the condom in the second package.

In another embodiment of my invention, I provide an article of manufacture comprising a condom shaped and dimensioned to fit an erect penis having a base and a head and a defined shape and dimension and length. The condom is shaped and dimensioned to, when installed on the erect penis, extend over substantially the entirety of the length of the penis such that the installed condom is free of a rolled portion at the base of the penis.

In a further embodiment of my invention, I provide an article of manufacture comprising a package; and, a condom folded in the package. The condom is folded in the package such that rolling of the condom to conform the condom to the package is unnecessary and is prevented. The condom is shaped and dimensioned to fit over an erect penis.

In still another embodiment of my invention, I provide an article of manufacture comprising a package; and, a condom stored in the package. The condom is shaped and dimensioned to fit over an erect penis. The erect penis includes a base and a head. The condom includes a flared portion shaped and dimensioned to conform to and fit over the base of the penis.

In yet another embodiment of my invention, I provide apparatus for selecting a condom size for an erect penis. The apparatus includes tool apparatus including a first scale having indicia for indicating the length of the erect penis;

and, a second scale having indicia for indicating the width of the erect penis. The apparatus can also include a plurality of packages each including at least one condom. Each of the packages includes indicia indicating the size of the condom in said package, and correlating the size of the condom to indicia on the first and second scales.

Turning now to the drawings, which depict the presently preferred embodiments of the invention for the purpose of illustrating the practice thereof and not by way of limitation of the scope of the invention, and in which like references characters refer to corresponding elements throughout the several views, FIG. 1 illustrates an elastic latex prophylactic, or condom, 13 installed on an erect penis 10. The prophylactic 13 includes a closed end 20 which fits over the distal end or head 11 of the penis 10. The prophylactic also includes an open end 14 which fits over the base 14 of penis 10. The length of erect penis 10 is indicated by arrows L. The greatest width of penis 10 is indicated by arrows W. When prophylactic 13 is installed on penis 10, the length of prophylactic 13 is indicated by arrows A and the width of prophylactic 13 is indicated by arrows B.

Figure 2:
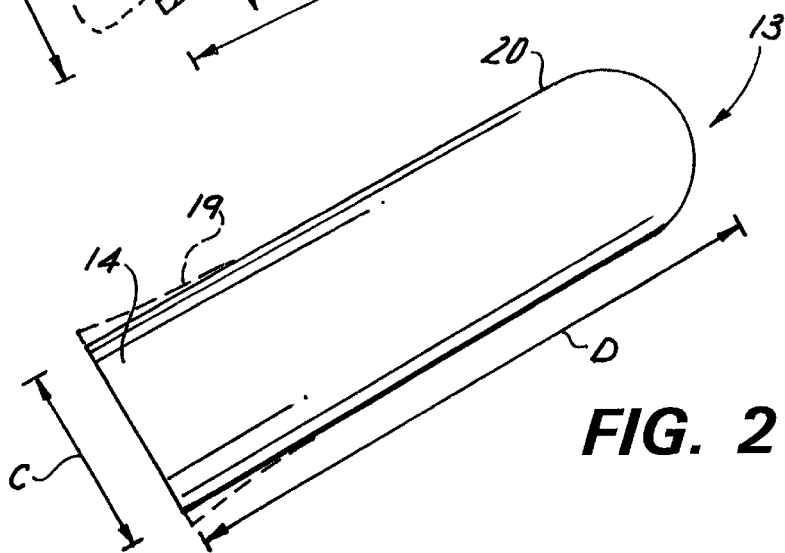
FIG. 2 is a side view further illustrating the prophylactic of FIG. 1.

As shown in FIG. 2, when prophylactic 13 is in its normal configuration and has not been installed on and conformed to the shape and dimension of penis 10, prophylactic 13 has a generally cylindrical hollow configuration. The open end 14 of prophylactic 13 can, if desired, have the flared shaped indicated by dashed lines 19 so that end 14 better conforms to the flared base 12 of penis 10. In FIG. 2, the length of prophylactic 13 is indicated by arrows D and the width by arrows C. The length D is generally equivalent to the length A after the prophylactic has been installed on an erect penis 10. The width C is generally less than the width B because prophylactic 13 preferably elastically expands to fit over erect penis 10. The elastic expansion of prophylactic 13 helps to produce a seal between penis 10 and the cylindrical portion of prophylactic 13 which extends over the sides and base of penis 10.

If desired, the open end 14 of prophylactic 13 can consist of latex having a thickness greater than that of the closed end 20 and sides of the prophylactic 13 extending between end 20 and end 14. End 14 can also, if desired, be ribbed. The inner surface of end 14 can, if desired, be coated with contact adhesive or other adhesive. One potential function of utilizing thicker latex, ribs, or adhesive on or in end 14 is to make end 14 more resistant to rolling up penis 10 away from base 12 toward head 11.

It is preferred that the length A of prophylactic 13 be equal to or somewhat less (typically preferably about 1% to 20% less) than the length L of penis 10. It is also preferred, but not required, that prophylactic 13 not be rolled in conventional fashion, but instead simply be folded and placed in a conventional square foil packet or other package. When utilized in conjunction with the fitting procedure described below, a prophylactic 13 which has not been rolled during packaging is believed to provide significantly more comfort and significantly less risk of rolling up than a conventional prophylactic.

In one preferred embodiment of the invention, prophylactics are provided in a variety of lengths. Each length is provided in a variety of widths or circumferences. Indicia identify the size, i.e., the length and circumference, of each condom. While the indicia can be imprinted or otherwise formed on the condom, they more commonly are printed on the package in which the condom is stored. Although any desired indicia can be utilized, one proposed system is shown below in Tables I and II.

TABLE I

Condom Length Indicia

| Length Indicia of Condom (mm) Indicia | Actual Length of Penis (mm) | Preferred Length As Indicated by Length |
|---|---|---|
| 5 | 90 | 80 to 90 |
| 6 | 115 | 91 to 115 |
| 7 | 140 | 116 to 140 |
| 8 | 165 | 141 to 165 |
| 9 | 190 | 166 to 190 |
| 10 | 215 | 191 to 215 |
| 11 | 240 | 216 to 240 |
| 12 | 265 | 241 to 265 |
| 13 | 290 | 266 to 290 |
| 14 | 315 | 291 to 315 |
| 15 | 340 | 316 to 340 |
| 16 | 365 | 341 to 365 |

TABLE II

Condom Width/Circumference Indicia*

| Width Indicia Circumference of | Actual Circumference of Condom | Maximum Erect Penis (mm) |
|---|---|---|
| A | 80 | 90 |
| B | 90 | 100 |
| C | 100 | 110 |
| D | 110 | 120 |
| E | 120 | 130 |
| F | 130 | 140 |
| G | 140 | 150 |
| H | 150 | 160 |

*Each length condom preferably is provided in each of the widths indicated in Table II. Consequently, a condom with a length of 11 is provided in each of the widths A to H so that there is a size 11A condom, size 11B condom, size 11C condom, size 11D condom, etc. To avoid discriminating against men with very short or very long penile lengths, it is intended that the invention provide prophylactics having lengths outside the currently approved FDA range.

By way of example, with reference to Tables I and II, when the indicia 11E appear on a package containing a condom or appear on a condom, then the condom has a length of 240 mm and a circumference of 120 mm. When the indicia 5G appear on a package containing a condom, then the condom has a length of 90 mm and a circumference of 140 mm. When the indicia 5B appear on a package containing a condom, the condom has a length of 90 mm and a circumference of 90 mm.

As noted in Table I, the length of a condom utilized in accordance with the invention preferably is equal to or less than the length of an erect penis to reduce the risk that the condom will tend to roll up and off the penis.

As noted in Table II, the actual width (or circumference) of a condom is preferably less than the width (or circumference) of an erect penis because the stretching of the condom to conform to an erect penis is important in creating a seal between the condom and penis and in maintaining the condom on the penis.

Figure 3:
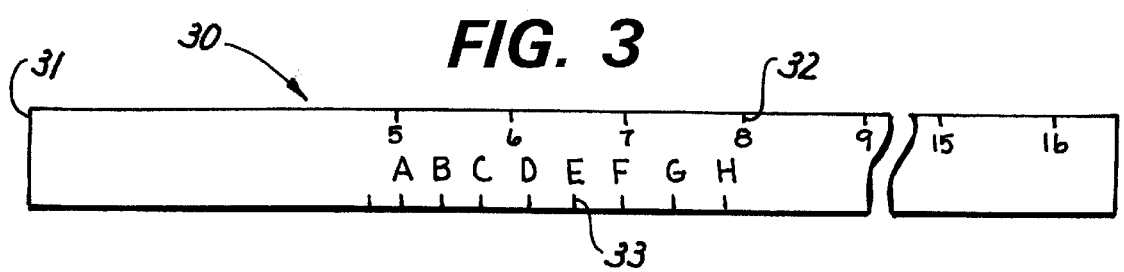
FIG. 3 is a top view of a pliable measuring tape utilized to determine the size of prophylactic utilized on an erect penis having a particular length and width.

FIG. 3 illustrates a pliable strip 30 of fabric, plastic, or other material which can be utilized to measure the size of an erect penis, to correlate the size with the condoms provided in accordance with Tables I and II above, and to enable the user to select an appropriate size condom. In use of the strip 30, end 31 is placed at the base of the user's erect penis and strip 30 is extended from the penis base to the tip of the penis. If, for example, the tip of the penis is at rule mark 32, then the length of the appropriate condom to be utilized by the user is indicated by indicia "8". The user then circumferentially wraps strip 30 around the portion of his erect penis having the greatest circumference. If, for example, the circumference of the user's erect penis is indicated by the distance from end 31 to rule mark 33, then the width of the appropriate condom to be utilized by the user is indicated by the indicia "E". The distance from end 31 to the rule mark 33 is 130 mm. The circumference of a condom with an "E" width indicia is only 120 mm. After measuring the length and circumference of his erect penis in the manner just described, the user selects a size 8E condom and draw it over his erect penis 10 to the position shown in FIG. 1. Since the circumference of the 8E condom is less than the circumference of the user's erect penis 10, the condom elastically stretches when pulled over penis 10.

One advantage of providing a condom with a flared open end 19 is that the flared end tends to stretch radially outwardly in the directions indicated by arrows S and T an amount which is about equal to the amounts that the side portions 22 and 23 of the condom stretch radially outwardly when the condom is installed on an erect penis 10. Such uniform stretching tends to avoid the tourniquet effect produced at the base 12 by the rolled portion of a conventional condom. Simply the fact that condom utilized in accordance with the presently preferred embodiment of the invention do not include a rolled portion also tends to eliminate the tourniquet effect produced by conventional condoms and to uniformly distribute along most of the length of erect penis 10 the compressive forces generated against penis 10 by elastically stretched condom 13.

Condom manufacturing machines typically utilize generally cylindrical rods which are dipped in liquid latex one or more times. The latex on each rod is allowed to cure and harden to form a prophylactic which is peeled off the rod. In order to produce a variety of condom sizes in accordance with the invention, a condom manufacturing machine is provided which includes removable, interchangeable dipping rods of differing shape and dimension. The rods are removably attached to the frame or panel which is displaced vertically up and down in order to dip the rods in a vat of liquid latex. Such removable and interchangeable dipping rods permit the efficient economic production of a vast array of prophylactics of differing width and length.

Having described my invention in such terms as to enable those of ordinary skill in the art to make and use the invention, and having described the presently preferred embodiments thereof, I claim:

1. An article of manufacture comprising a plurality of packages each including at least one condom,
   (a) at least a first one of said packages including
       (i) first length indicia indicating the length of the condom in said package, and
       (ii) first width indicia different from said length indicia and indicating the width of the condom in said package; and,
   (b) at least a second one of said packages including
       (i) second length indicia indicating the length of the condom in said second one of said packages, and
       (ii) second width indicia different from said length indicia on said second one of said packages and indicating the width of the condom in said second one of said packages;
   said first length indicia being different from said second length indicia and said first width indicia being different from said second width indicia to indicate that the length and width of the condom in said first package is different from the length and width of the condom in said second package.

2. The article of manufacture of claim 1 including a third one of said packages including
   (i) third length indicia indicating the length of the condom in said third one of said packages, and
   (ii) third width indicia indicating the width of the condom in said third one of said packages;
   said third length indicia being equal to said second length indicia and said third width indicia being different from said second width indicia to indicate that the length of the condom in said third package is the same as the length of the condom in said second package and that the width of the condom in said third package differs from the width of the condom in said second package.

3. The article of manufacture of claim 1 including a fourth one of said packages including
   (i) fourth length indicia indicating the length of the condom in said fourth one of said packages, and
   (ii) fourth width indicia indicating the width of the condom in said fourth one of said packages;
   said fourth length indicia being different from said second length indicia and said fourth width indicia being equal to said second width indicia to indicate that the length of the condom in said fourth package differs from the length of the condom in said second package and that the width of the condom in said fourth package is the same as the width of the condom in said second package.

\* \* \* \* \*